US008016825B2

(12) United States Patent
Okada

(10) Patent No.: US 8,016,825 B2
(45) Date of Patent: Sep. 13, 2011

(54) RADIO KNIFE

(75) Inventor: Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 612 days.

(21) Appl. No.: 10/823,814

(22) Filed: Apr. 14, 2004

(65) Prior Publication Data

US 2004/0210284 A1 Oct. 21, 2004

(30) Foreign Application Priority Data

Apr. 17, 2003 (JP) .................................. 2003-113164

(51) Int. Cl.
*A61B 18/14* (2006.01)
(52) U.S. Cl. ....................................................... 606/45
(58) Field of Classification Search ............... 606/32–50
See application file for complete search history.

(56) References Cited

U.S. PATENT DOCUMENTS

| | | | | |
|---|---|---|---|---|
| 4,943,290 A | * | 7/1990 | Rexroth et al. ................. | 606/45 |
| 5,846,241 A | * | 12/1998 | Kittur et al. .................... | 606/48 |
| 2002/0198520 A1 | * | 12/2002 | Coen et al. ..................... | 606/41 |

FOREIGN PATENT DOCUMENTS

| | | | |
|---|---|---|---|
| JP | 4-329944 | * | 11/1992 |
| JP | 2000-135221 | | 5/2000 |
| JP | 2002-28166 | | 1/2001 |
| JP | 2002-301088 | | 10/2002 |

OTHER PUBLICATIONS

Tuneo Oyama et al., "Endoscopic Mucosal Resection Using a Hooking Knife", Stomach and Intestine (2002), vol. 37, No. 9, pp. 1155-1161, together with English-language translation.
Haruhiro Inoue et al., "Endoscopic Mucosal Resection with a Cap-fitted Panendoscope for Stomach Cancer", Endoscopia Digestiva (2002), vol. 14, No. 9, pp. 1301-1302, together with English-language translation.

* cited by examiner

*Primary Examiner* — Linda Dvorak
*Assistant Examiner* — Ronald Hupczey, Jr.
(74) *Attorney, Agent, or Firm* — Scully, Scott, Murphy & Presser, P.C.

(57) ABSTRACT

An electrode portion is provided with a rod-shaped portion extending in the direction of a flexible sheath. An insulating tip which closes the distal end portion of the sheath is provided with a slide hole and openings for liquid feed. The rod-shaped portion is passed through the sheath for axial movement, and cannot get into the openings.

8 Claims, 4 Drawing Sheets

RADIO KNIFE

CROSS-REFERENCE TO RELATED APPLICATIONS

This application is based upon and claims the benefit of priority from prior Japanese Patent Application No. 2003-113164, filed Apr. 17, 2003, the entire contents of which are incorporated herein by reference.

BACKGROUND OF THE INVENTION

1. Field of the Invention

The present invention relates to a radio knife (diathermic cutter) for resecting a living tissue by high-frequency incision.

2. Description of the Related Art

Conventionally, a living tissue, such as a mucous membrane, is resected by means of a surgical instrument that is inserted into a patient's body through a channel of an endoscope after the endoscope has been inserted into the body. A high-frequency surgical instrument, such as the one described in Jpn. Pat. Appln. KOKAI Publication No. 4-329944 (Patent Document 1), is used for the resection.

The high-frequency surgical instrument described in Patent Document 1 has an elongated insertion section and a control section on the manipulation side. The insertion section is inserted into a patient's body through a channel of an endoscope. The control section is coupled to the proximal end portion of the insertion section. The insertion section has a flexible tube and an operating wire. The operating wire is inserted into the flexible tube for axial movement. A needle-shaped knife element (electrode portion) that extends in the axial direction is provided on the distal end portion of the operating wire. The control section is provided with an operating handle. The operating wire is moved in the axial direction by manipulating the handle. A high-frequency current can be supplied to the knife element.

As the operating handle is manipulated, the operating wire is moved in the axial direction. The operating wire serves to move the knife element from a storage position to an operating position. In the storage position, the knife element is confined to the flexible tube. In the operating position, the knife element projects from the flexible tube. If a high-frequency current is supplied to the knife element in the operating position outside the flexible tube, the knife element cauterizes and incises a living tissue that it touches.

Further, the high-frequency surgical instrument described in Patent Document 1 is provided with liquid feed means that is used to feed a liquid, such as a drug solution, to the proximal end portion of the insertion section. The drug solution or the like can be supplied from the liquid feed means to the distal end side of the flexible tube through its bore and discharged through a distal opening of the tube.

As a publicly-known non-patent document, there is Non-patent Document 1: Tuneo Oyama, et al., "Extended Adaptation of Stomach EMR: Contrivance and Results of Method Aimed at Large En-block Resection; Endoscopic Mucosal Resection Using a Hooking Knife", Stomach and Intestine, August 2002, Vol. 37, No. 9, pp. 1155-1161. The Non-patent Document 1 discloses a high-frequency treatment instrument having a structure different from that disclosed in Patent Document 1. The high-frequency treatment instrument has a bent portion made by bending a distal end of its needle-shaped knife section (electrode section). In use of the high-frequency treatment instrument, a living tissue is hooked onto the bent portion of the knife section, and cauterized and incised while being pulled up by the bent portion.

As another publicly-known non-patent document, there is Non-patent Document 2: Haruhiro Inoue et al., "Endoscopic Mucosal Resection with a Cap-fitted Panendoscope for Stomach Cancer", Endoscopia Digestiva, A to Z for How to Select Endoscopic Treatment Tools, September 2002, Vol. 14, No. 9, pp. 1301-1302. The Non-patent Document 2 discloses a high-frequency treatment instrument having another structure. The high-frequency treatment instrument has a disc-shaped electrode portion at a distal end of a needle-shaped knife section (electrode section). In use of the high-frequency treatment instrument, a living tissue is hooked onto the disk-shaped electrode portion of the knife section, and cauterized and incised while being pulled up by the disk-shaped electrode portion.

If the living tissue is incised with use of either of these high-frequency surgical instruments, an incised region sometimes may bleed in the course of the incision. In this case, each instrument carries out the following processes of treatment. First, in the case of the high-frequency surgical instrument described in Patent Document 1, the working instrument is temporarily taken out of the channel of the endoscope. Thereafter, another surgical instrument for blood stanching is inserted into the channel of the endoscope, and hemostatic treatment is carried out. When bleeding has stopped, the high-frequency instrument of Patent Document 1 is inserted again into the channel of the endoscope, and the treatment is continued.

In the cases of the high-frequency surgical instruments described in Non-patent Literature 1 and 2, the bent portion on the distal end of the knife element or the distal end face of the disc is pressed against a bleeding point to supply high-frequency current to it. Thus, blood from the bleeding point can be coagulated so that bleeding is stopped.

BRIEF SUMMARY OF THE INVENTION

According to the present invention, there is provided a radio knife, which comprises: an electrically insulative flexible sheath having a distal end portion and a proximal end portion, the distal end portion of the sheath having a distal opening and an axis; an electrically insulative insulating tip which closes the distal opening of the sheath, the insulating tip having a slide hole with a diameter smaller than that of the distal opening extending along the axis thereof; an operating wire axially movable in the sheath; an electrode portion which has a distal end portion and a proximal end portion and of which at least a part forms a rod-shaped portion, the proximal end portion of the electrode portion being coupled to the operating wire, the rod-shaped portion being passed through the slide hole for axial projection and retraction; a control section which is provided on the proximal end portion of the sheath and controls the operating wire to project and retract the electrode portion in the axial direction, the control section having a high-frequency current supply portion which supplies a high-frequency current to the electrode portion; a liquid feed portion which is provided on the proximal end side of the sheath and feeds a liquid into the sheath; and openings for liquid feed which are formed in the insulating tip and prevent the rod-shaped portion from inserting therein.

Preferably, the sheath has a single bore which is inserted in the operating wire.

Preferably, the insulating tip is located so that the openings for liquid feed communicate with the slide hole.

Preferably, the slide hole of the insulating tip is formed of a polygonal opening in which the rod-shaped portion is inscribed, the other parts of the polygonal opening than that part which is occupied by the rod-shaped portion forming the openings for liquid feed.

Preferably, the insulating tip is formed having a plurality of straight openings extending radially outward from the slide hole, the respective inner end portions of the openings being coupled to the slide hole, each of the straight openings having a width such that the opening cannot be penetrated by the electrode portion.

Preferably, the openings for liquid feed in the insulating tip are arranged around and independently of the slide hole.

Preferably, the sheath has an extending portion extending ahead of the insulating tip, the extending portion having an internal space which stores the electrode portion.

Preferably, the electrode portion has an extending portion located on the distal end portion of the rod-shaped portion and extending across the extending direction of the rod-shaped portion.

Preferably, the extending portion is a hooked bent portion extending substantially at right angles to the distal end portion of the rod-shaped portion.

Preferably, the extending portion is a platelike electrode portion coupled to the distal end portion of the rod-shaped portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1A:
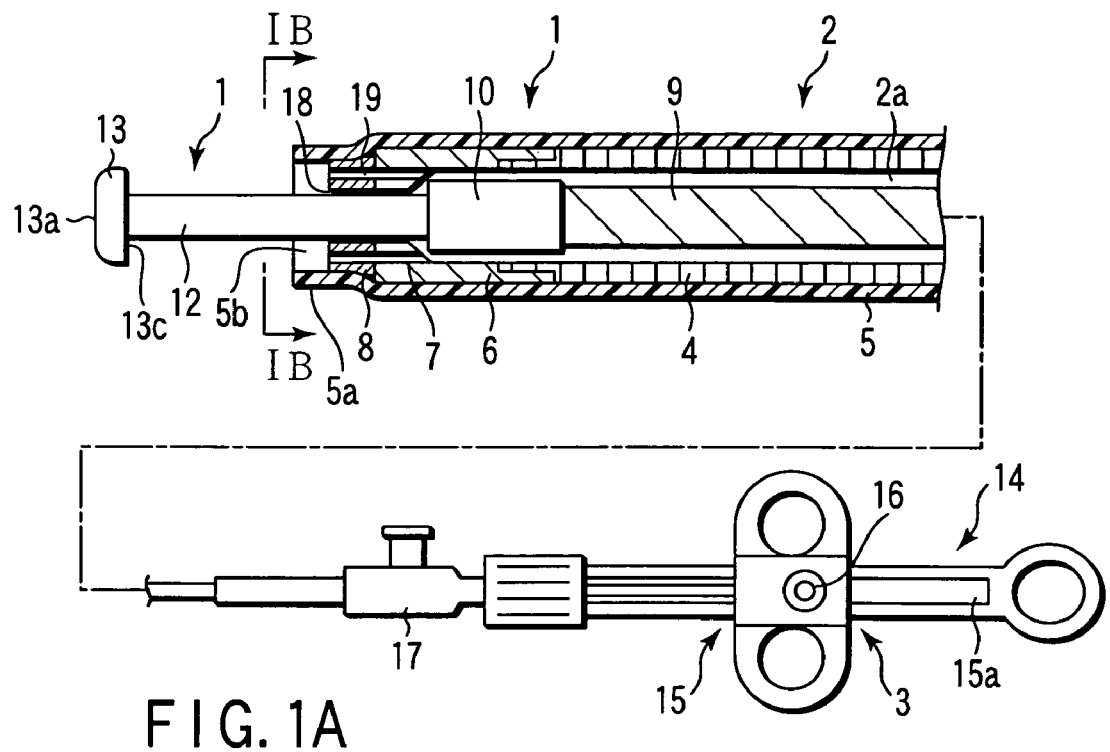
FIG. 1A is a longitudinal sectional view showing an outline of the principal part of a radio knife according to a first embodiment of the invention.

A first embodiment of the present invention will now be described with reference to FIGS. 1A to 6. FIG. 1A shows an outline of a radio knife 1 of the present embodiment. The knife 1 comprises a flexible, elongated sheath 2 and a control section 3 on the proximal end of the sheath 2. The sheath 2 can be passed through a channel (not shown) of an endoscope. The sheath 2 is composed of, for example, a closely-wound coil 4 and an insulating tube 5 that covers the outer periphery of the coil 4. The tube 5 is formed of, for example, tetrafluoroethylene. The proximal end portion of a cylindrical stopper member 6 is fitted on and connected to the distal end of the coil 4. The outer periphery of the stopper member 6 is covered by the distal end portion of the insulating tube 5 so as to be flush with the outer peripheral surface of the coil 4.

A thick-walled portion 7 protrudes inward from the inner peripheral surface of the stopper member 6 on its distal end side. It is formed in a manner such that the distal end portion of the stopper member 6 is made thicker inside than its proximal end portion with respect to the radial direction. A ring-shaped insulating tip (electrode supporting portion) 8 is located on the distal end side of the thick-walled portion 7.

Figure 2:
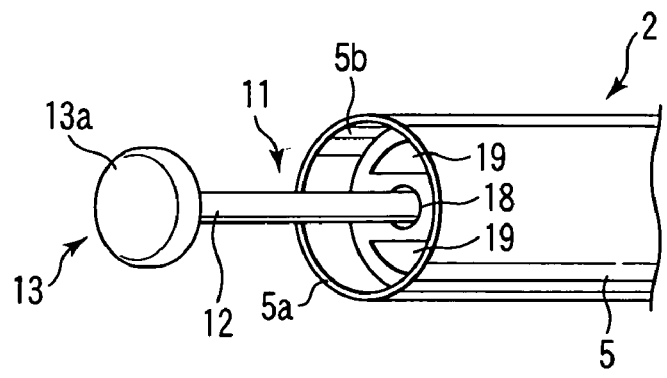
FIG. 2 is a perspective view showing the distal end portion of the radio knife according to the first embodiment.
Figure 3:
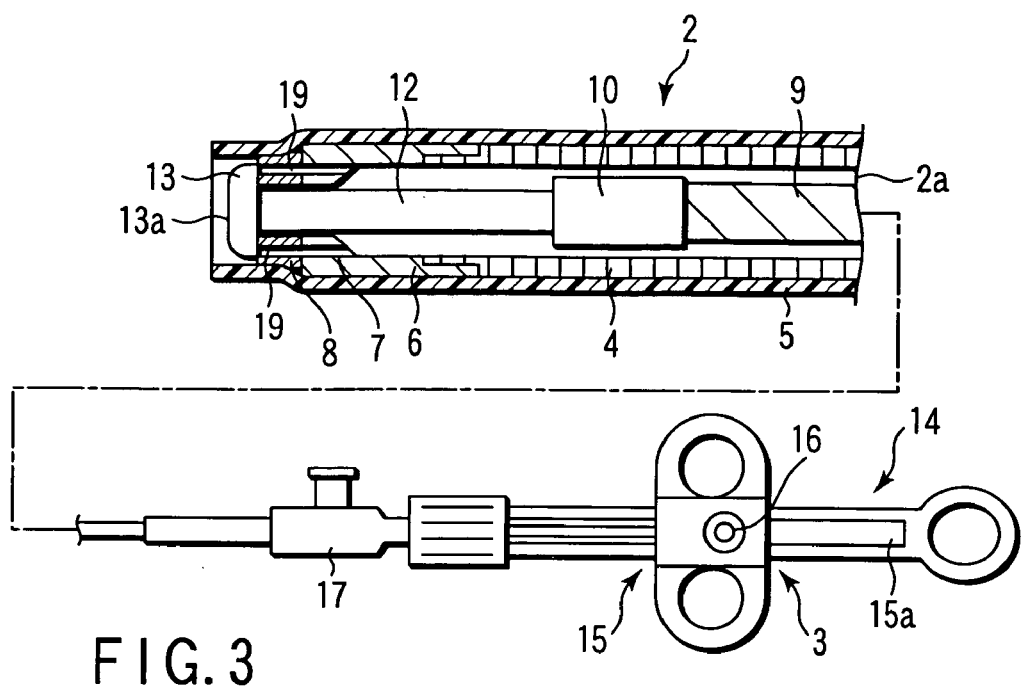
FIG. 3 is a longitudinal sectional view showing a knife element of the radio knife of the first embodiment, confined to a sheath.

The inner peripheral side of the insulating tip 8 is formed substantially flush with the inner peripheral surface of the thick-walled portion 7. The outer peripheral side of the tip 8 is covered by the insulating tube 5. As shown in FIG. 2, moreover, the distal end portion of the insulating tube 5 is formed having a distal extending portion 5a that extends forward beyond the distal end of the insulating tip 8. The internal space of the extending portion 5a of the tube 5 forms an electrode storage portion 5b. As shown in FIG. 3, a platelike electrode portion 13 of a knife element 11 (mentioned later) is held in the storage portion for projection and retraction.

An electrically conductive operating wire 9 is passed through the sheath 2 for axial movement. An electrically conductive stopper receiving portion 10 to engage the thick-walled portion 7 of the stopper member 6 is fitted on the distal end portion of the wire 9.

The knife element (electrode portion) 11 shown in FIG. 2 is connected to the stopper receiving portion 10 on the distal end of the operating wire 9. The knife element 11 has a rod-shaped electrode portion 12 and the platelike electrode portion 13 in the form of a disc. The electrode portion 13 is coupled to the distal end of the electrode portion 12. The electrode portions 12 and 13 are integrally formed of an electrically conductive material. The platelike electrode portion 13 has a circular distal flat portion 13a, which is contained by a plane substantially perpendicular to the axis of the electrode portion 12. The proximal end portion of rod-shaped electrode portion 12 is fixed and connected electrically to the stopper receiving portion 10.

The control section 3 of the radio knife 1 comprises a control section body 14 substantially in the form of a shaft and a slider 15. The control section body 14 has a guide grove 15a for the slider 15, which extends in its axial direction. The slider 15 is fitted on the body 14 so as to be slidable in the axial direction.

The control section body 14 is formed having a passage hole (not shown) through which the operating wire 9 is passed. The proximal end portion of the wire 9 extends rearward through the passage hole of the control section body 14 and is coupled to the slider 15. As the slider 15 is slid in the axial direction, the wire 9 moves axially in the bore of the sheath 2. As the wire 9 moves in this manner, the rod-shaped electrode portion 12 of the knife element 11 can be projected and retracted from the distal end portion of the sheath 2.

A connector portion 16 protrudes from the slider 15. It has internal and external terminal areas. A cord (not shown) that leads to a high-frequency generator (not shown) is connected electrically to the external terminal area of the connector portion 16. The proximal end portion of the operating wire 9 is connected electrically to the internal terminal area of the connector portion 16. Thus, the platelike electrode portion 13 of the knife element 11 is connected electrically to the connector portion 16 of the slider 15 through the rod-shaped electrode portion 12, stopper receiving portion 10, and operating wire 9.

Further, a cock 17 for use as liquid feed means is provided on the proximal end portion of the sheath 2. As shown in FIG. 5B, the cock 17 is removably fitted with a syringe 20 that contains a liquid, such as a physiological saline solution. The liquid that is fed under pressure from the syringe 20 can be injected into an internal space 2a of the sheath 2 through the cock 17.

Figure 1B:
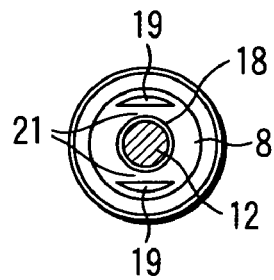
FIG. 1B is a sectional view taken along line IB-IB of FIG. 1A.

As shown in FIG. 1B, a slide aperture 18 is formed axially in the stopper member 6 and the insulating tip 8. The rod-shaped electrode portion 12 of the knife element 11 is passed through the slide aperture 18. Further, a pair of liquid feed openings 19 are arranged around the slide aperture 18. The openings 19 communicate with the internal space 2a of the sheath 2. The openings 19 are isolated from each other by the slide aperture 18 and partition walls 21, and are located independently of the aperture 18. The liquid that is injected through the cock 17 can be ejected from the liquid feed openings 19 through the internal space 2a of the sheath 2.

The following is a description of the operation of the radio knife 1 of the present embodiment constructed in this manner. The way of using the knife 1 will be described first. In working the knife 1, the slider 15 and the body 14 of the control section 3 are grasped. Then, the slider 15 of the control section 3 is axially moved with respect to the control section body 14, whereupon the knife element 11 is moved in the axial direction by means of the operating wire 9. If the slider 15 is moved rearward (or toward the proximal end) with respect to the control section body 14, the operating wire 9 moves rearward. As this is done, the rod-shaped electrode portion 12 of the knife element 11 moves in a direction such that it is drawn into the sheath 2. Thereupon, a proximal end face 13c of the platelike electrode portion 13 is brought into contact with the insulating tip 8 on the distal end of the sheath 2, as shown in FIG. 3. In this state, the electrode portion 13 is held in the storage portion 5b. The radio knife 1 is mostly kept set in this manner when it is inserted into the channel of the endoscope without requiring operation of the knife element 11.

If the slider 15 is moved forward (or toward the distal end) with respect to the control section body 14, moreover, the operating wire 9 moves forward. As this is done, the rod-shaped electrode portion 12 projects outward from the distal end of the sheath 2, whereupon the proximal end face 13c of the platelike electrode portion 13 is disengaged forward from the distal end of the sheath 2. The knife element 11 is used to resect a mucous membrane in this state after it is energized.

Figures 4A, 4B:
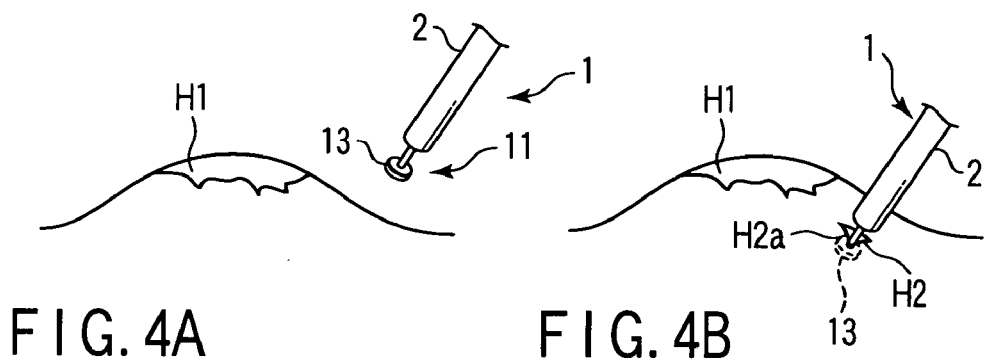
FIG. 4A is a perspective view showing the distal end portion of the radio knife of the first embodiment, located close to an affected mucosal region to be resected in the body cavity.
FIG. 4B is a perspective view showing the way first incision is carried out to bore a mucous membrane around the affected mucosal region.

The operation for the resection of the mucous membrane in a patient's body cavity with use the radio knife 1 will now be described with reference to FIGS. 4A to 6. In this case, the knife 1 is inserted into the channel of the endoscope that is inserted in advance into the patient's body. First, an injection needle (not shown) is introduced into the body cavity through the channel of the endoscope (not shown). Then, the needle is stuck into the submucosa of an affected mucosal region H1, a target region to be resected in the body cavity, as shown in FIG. 4A. In this state, the saline solution is injected into the submucosa of the affected mucosal region H1 through the needle, whereby the portion H1 is swollen.

Subsequently, a patient plate (not shown) is put on the patient's body. Thereafter, the radio knife 1 of the present embodiment is introduced into the body cavity through the channel of the endoscope. When this is done, the knife element 11 is kept retracted in the sheath 2.

Thereafter, the sheath 2 of the radio knife 1 is projected from the channel of the endoscope, and the knife 1 is brought close to the target region to be resected. Subsequently, the knife element 11 of the knife 1 is projected from the distal end of the sheath 2, as shown in FIG. 4A. In this state, a first incision is carried out such that a hole H2 is bored in the mucous membrane that surrounds the affected mucosal region H1, as shown in FIG. 4B.

Figures 4C, 4D:
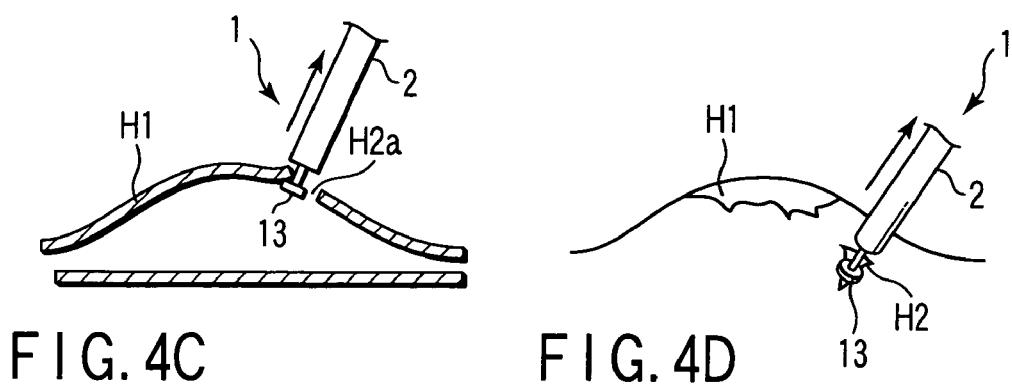
FIG. 4C is a profile showing a mucous membrane hooked up by means of a platelike electrode portion.
FIG. 4D is a perspective view showing the way an affected mucosal region is incised by means of the knife element.

As shown in FIG. 4C, thereafter, the platelike electrode portion 13 is hitched to a part of a peripheral edge region H2a of the hole H2. In this state, the knife element 11 is moved in the longitudinal direction (or the axial direction of the rod-shaped electrode portion 12). Thereupon, the electrode portion 13 hooks up the mucous membrane. If a high-frequency current is then supplied to the knife element 11, the mucous membrane is incised by the proximal end face 13c of the electrode portion 13, as shown in FIG. 4D. By repeating this operation, the mucous membrane that surrounds the affected mucosal region H1 is incised all around.

Figure 5A:
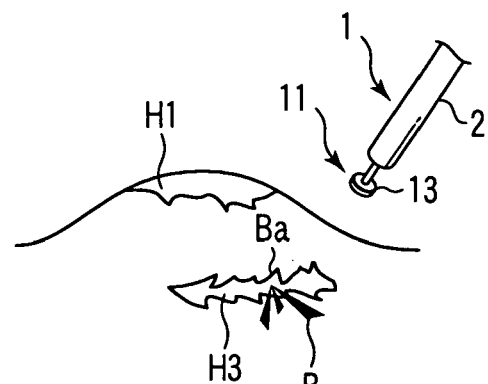
FIG. 5A is a perspective view showing bleeding from an incised region recognized in the course of the incision with the radio knife of the first embodiment.
Figure 5B:
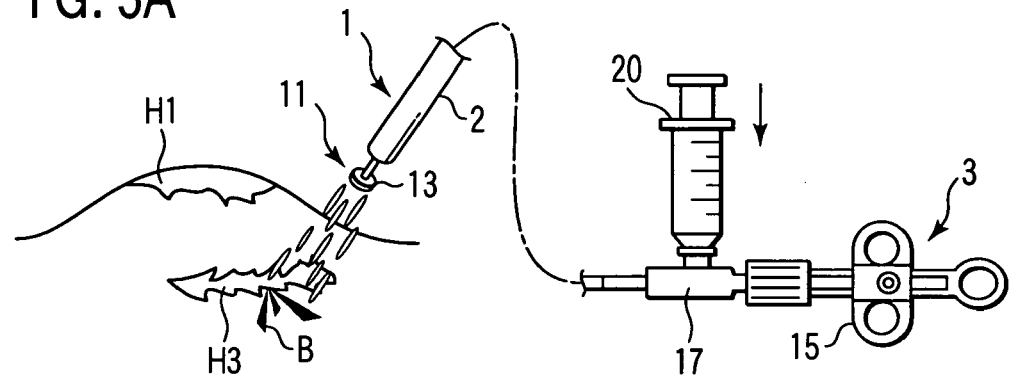
FIG. 5B is a perspective view illustrating the way of cleaning a bleeding region during use of the radio knife of the first embodiment.
Figure 5C:
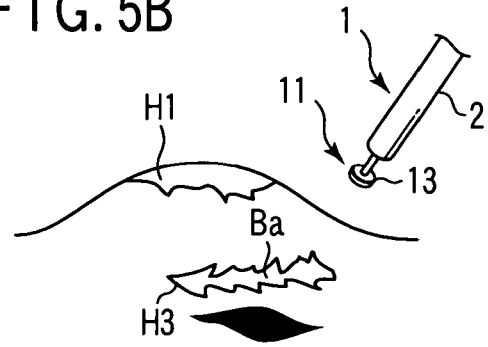
FIG. 5C is a perspective view showing the way a bleeding point is exposed after the bleeding region is cleaned during use of the radio knife of the first embodiment.
Figure 5D:
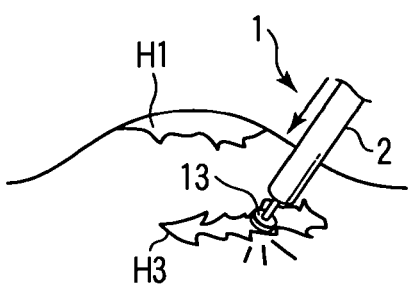
FIG. 5D is a perspective view illustrating the way of coagulating the bleeding point and stanching the flow of blood.

If bleeding B from the incised region is detected in the course of the incision, as shown in FIG. 5A, a hemostatic operation is carried out in the following manner. In starting this hemostatic operation, the syringe 20 that contains a physiological saline solution, for example, is attached to the cock 17, as shown in FIG. 5B. The saline solution that is delivered under pressure from the syringe 20 is injected into the internal space 2a of the sheath 2 through the cock 17. The saline solution is ejected through the openings 19 at the distal end and used to clean the bleeding region. Thereupon, a bleeding point Ba is exposed, as shown in FIG. 5C, so that the distal flat portion 13a of the platelike electrode portion 13 of the radio knife 1 is pressed against the bleeding point Ba to energize it, as shown in FIG. 5D. Thus, blood from the bleeding point Ba is coagulated so that bleeding is stopped.

Figure 6:
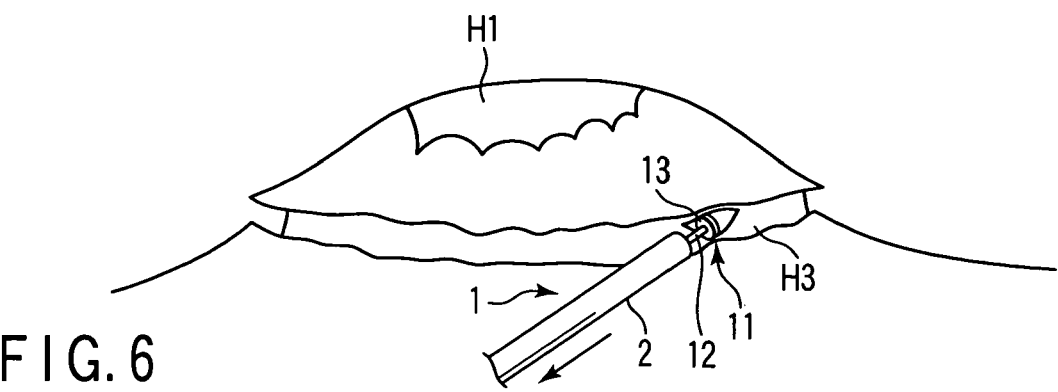
FIG. 6 is a perspective view illustrating the way the affected mucosal region is gradually incised and exfoliated with the knife element held against an incision formed around the mucosal region by use of the radio knife of the first embodiment.

In this manner, the mucous membrane that surrounds the affected mucosal region H1 is entirely incised throughout the circumference. Thereafter, the knife element 11 is held against an incision H3 that is formed when the mucous membrane around the region H1 is incised, as shown in FIG. 6. In this state, the platelike electrode portion 13 is hooked up so that the region H1 is gradually incised and exfoliated. After the whole affected mucosal region H1 is resected, the resulting resected piece of the region H1 is held by means of grasping forceps (not shown) or the like. Thereafter, the resected piece, along with the forceps, is taken out of the patient's body through the channel of the endoscope, whereupon treatment is finished.

The configuration described above has the effects described below. Specifically, in the radio knife 1 according to the present embodiment, the slide aperture 18 through which the rod-shaped electrode portion 12 is passed is formed axially in the stopper member 6 and the insulating tip 8. Further, the two openings 19 for liquid feed that communicate with the internal space 2a of the sheath 2 are arranged around the slide aperture 18. Therefore, the slide aperture 18 can be formed having substantially the same diameter with the electrode portion 12 of the knife element 11. Thus, the electrode portion 12 can be securely supported by means of the insulating tip 8, so that it can be prevented from oscillating.

According to the present embodiment, moreover, the stopper member 6 and the insulating tip 8 are provided with the two openings 19 for liquid feed. Therefore, the physiological saline solution that is fed from the syringe 20 can be injected into the internal space 2a of the sheath 2 through the cock 17 and ejected through the distal openings 19 to be used for cleaning the bleeding region. Accordingly, the bleeding region can be cleaned to expose the bleeding point without changing the surgical instrument before blood is coagulated and stanched by means of the distal flat portion 13a of the platelike electrode portion 13. Thus, intra-operative bleeding can be stopped quickly and securely.

Figure 7A:
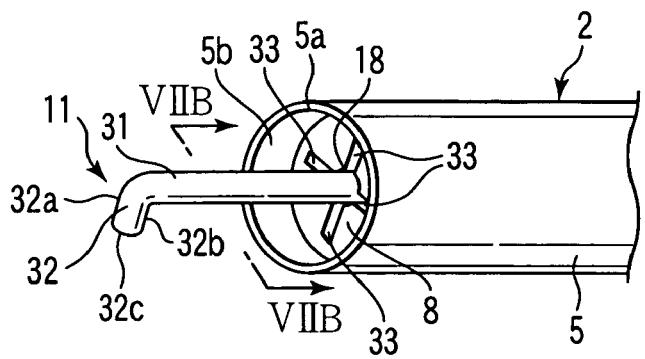
FIG. 7A is a perspective view showing the distal end portion of a radio knife according to a second embodiment of the invention.
Figure 7B:
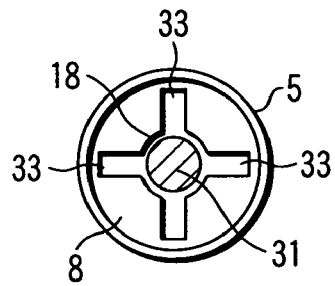
FIG. 7B is a sectional view taken along line VIIB-VIIB of FIG. 7A.

FIGS. 7A and 7B show a second embodiment of the present invention. According to the present embodiment, the configuration of the radio knife 1 of the first embodiment (see FIGS. 1A to 6) is modified in the following manner. The second embodiment shares other configurations with the first embodiment. Like numerals are used to designate like portions of the radio knives of the two embodiments, and a description of those portions is omitted.

In the present embodiment, as shown in FIG. 7A, a knife element 11 of the radio knife 1 has a rod-shaped electrode portion 31 and a bent portion 32. The bent portion 32 is formed on the distal end of the electrode portion 31 so as to extend substantially at right angles thereto.

As shown in FIG. 7B, moreover, a stopper member 6 and an insulating tip 8 are formed having four substantially cruciform, straight openings 33. The openings 33 extend radially outward from a slide aperture 18. The inner end portion of each opening 33 is coupled to the slide aperture 18. Further, the width of each opening 33 is set to a dimension such that it cannot be penetrated by either of the electrode portions 31 and 32.

The following is a description of the operation of the radio knife 1 of the present embodiment. A description of the same processes of operation of the first embodiment is omitted. If the slider 15 of the control section 3 is moved rearward (or toward the proximal end) with respect to the control section body 14 in working the knife 1, the operating wire 9 moves rearward. As this is done, in the present embodiment, the rod-shaped electrode portion 31 of the knife element 11 is drawn into a sheath 2. Thereupon, a proximal end face 32b of the bent portion 32 engages the insulating tip 8 of the sheath 2, and the bent portion 32 is held in the storage portion 5b at the distal end of the sheath 2.

In incising the affected mucosal region H1, moreover, it is hoisted and energized with the bent portion 32 of the knife element 11 hitched to the peripheral edge portion H2a of the hole H2 in the mucous membrane that surrounds the affected mucosal region H1. If bleeding B from the incised region is detected in the course of the incision, the syringe 20 that contains a physiological saline solution, for example, is attached to the cock 17. The saline solution that is delivered under pressure from the syringe 20 is injected into the internal space 2a of the sheath 2 through the cock 17 and ejected through the openings 33 at the distal end and used to clean the bleeding region. In stanching the flow of blood from the bleeding region, furthermore, a distal end face 32a of the bent portion 32 of the knife element 11 is pressed against the bleeding point Ba to energize it. The second embodiment shares other processes of operation with the first embodiment.

In the present embodiment, the openings 33 are coupled to the slide aperture 18 in which the rod-shaped electrode portion 31 of the knife element 11 moves. Therefore, the area of the openings 33 can be widened, so that the delivery of the liquid from the openings 33 can be increased.

In the present embodiment, moreover, the width of each opening 33 is set to a dimension such that it cannot be penetrated by either of the electrode portions 31 and 32. If the openings 33 are coupled to the periphery of the slide aperture 18, therefore, the electrode portion 31 of the knife element 11 cannot get into the openings 33. In consequence, the electrode portion 31 can be held substantially in the center of the sheath 2. Thus, a distal end portion 32c of the bent portion 32 never projects outward from the storage portion 5b when the bent portion 32 is held in the storage portion 5b, so that there is no possibility of its damaging the channel of the endoscope as the bent portion 32 is inserted into the channel. The second embodiment shares other effects with the first embodiment.

Figure 8A:
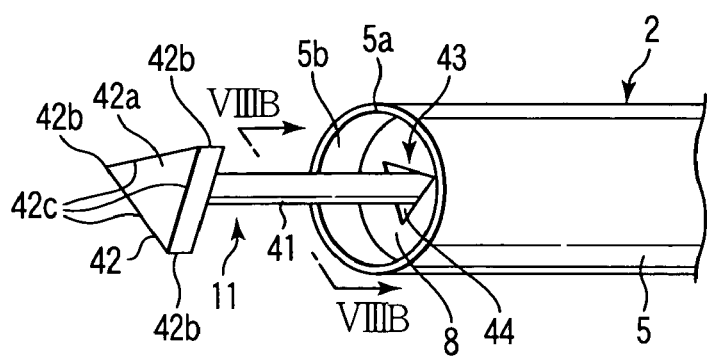
FIG. 8A is a perspective view showing the distal end portion of a radio knife according to a third embodiment of the invention.
Figure 8B:
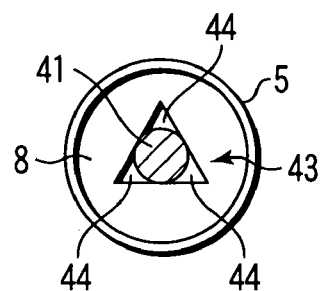
FIG. 8B is a sectional view taken along line VIIIB-VIIIB of FIG. 8A.

FIGS. 8A and 8B show a third embodiment of the present invention. According to the present embodiment, the configuration of the radio knife 1 of the first embodiment (see FIGS. 1A to 6) is modified in the following manner.

In a radio knife 1 of the present embodiment, as shown in FIG. 8A, a knife element 11 is formed of a rod-shaped electrode portion 41 and a substantially triangular platelike electrode portion 42. The electrode portion 42 is coupled to the distal end of the electrode portion 41. The platelike electrode portion 42 has a distal flat portion 42a, which is contained by a plane substantially perpendicular to the axis of the electrode portion 41, three sharp corner portions 42b, and edge portions 42c.

Further, a triangular aperture 43 into which the rod-shaped electrode portion 41 is inserted for advance and retreat is formed in the distal end of a sheath 2. As shown in FIG. 8B, the aperture 43 is a triangular hole in which the rod-shaped electrode portion 41 is inscribed, as shown in FIG. 8B. The other parts of the aperture 43 than that part which is occupied by the electrode portion 41 form openings 44, individually. The platelike electrode portion 42 is adjusted to a size such that cannot penetrate the triangular aperture 43.

Thus, according to the present embodiment, the distal end of the sheath 2 is provided with the triangular aperture 43 in which the rod-shaped electrode portion 41 is inscribed, and the other parts of the aperture 43 than that part which is occupied by the electrode portion 41 form the openings 44, as shown in FIG. 8B. Accordingly, the electrode portion 41 is situated in the center of the sheath 2 without the possibility of shifting its position. In consequence, the three sharp corner portions 42b of the triangular platelike electrode portion 42 never project outward from a storage portion 5b when the electrode portion 42 is held in the storage portion 5b, so that there is no possibility of their damaging the channel of the endoscope as the electrode portion 42 is inserted into the channel. The third embodiment shares other effects with the first embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A radio knife comprising:
   an electrically insulative flexible sheath having a flow channel inside, a distal end portion and a proximal end portion, the distal end portion of the sheath having a distal opening and an axis;
   a support member which closes the distal opening of the sheath, the support member having a slide hole with a diameter smaller than that of the distal opening extending along the axis thereof;
   an operating wire axially movable in the sheath;
   an electrode portion which has a distal end portion and a proximal end portion and of which at least a part forms a rod-shaped portion, the proximal end portion of the electrode portion being coupled to the operating wire, the rod-shaped portion being passed through the slide hole for axial projection and retraction;
   a control section which is provided on the proximal end portion of the sheath and controls the operating wire to project and retract the electrode portion in the axial direction, the control section having a high-frequency current supply portion which supplies a high-frequency current to the electrode portion;
   a liquid feed portion which is provided on the proximal end side of the sheath and feeds a liquid through the flow channel inside the sheath towards the distal opening; and
   a plurality of rectangular openings extending outward from the slide hole, an inner end portion of each of the rectangular openings being in communication with the slide hole and another end of each of the rectangular openings comprising a wall formed entirely in the support member, wherein an entire width of each of the plurality of rectangular openings is set to a dimension such that it cannot be penetrated by the electrode portion.

2. A radio knife according to claim 1, wherein the sheath has an extending portion extending ahead of the support member, the extending portion having an internal space which stores the electrode portion.

3. A radio knife according to claim 1, wherein the electrode portion has an extending portion located on the distal end portion of the rod-shaped portion and extending across the extending direction of the rod-shaped portion.

4. A radio knife according to claim 3, wherein the extending portion is a hooked bent portion extending substantially at right angles to the distal end portion of the rod-shaped portion.

5. A radio knife according to claim 3, wherein the extending portion is a platelike electrode portion coupled to the distal end portion of the rod-shaped portion.

6. A radio knife according to claim 1, wherein the sheath has an extending portion which is made to extend in front of the support member, and the extending portion has an internal space with contains the electrode portion.

7. A radio knife comprising:
   an electrically insulative flexible sheath having a flow channel inside, a distal end portion and a proximal end portion, the distal end portion of the sheath having a distal opening and an axis;
   a support member which closes the distal opening of the sheath;
   an operating wire axially movable in the sheath;
   an electrode portion which has a distal end portion and a proximal end portion and of which at least a part forms a rod-shaped portion, the proximal end portion of the electrode portion being coupled to the operating wire, the rod-shaped portion being passed through the slide hole for axial projection and retraction;
   a control section which is provided on the proximal end portion of the sheath and controls the operating wire to project and retract the electrode portion in the axial direction, the control section having a high-frequency current supply portion which supplies a high-frequency current to the electrode portion;
   a liquid feed portion which is provided on the proximal end side of the sheath and feeds a liquid through the flow channel inside the sheath towards the distal opening; and
   wherein a triangular aperture into which the rod-shaped electrode portion is inserted for advance and retreat is formed in the distal end of the sheath, said triangular aperture is a triangular hole in which the rod-shaped electrode portion is inscribed, and parts of said triangular aperture other than that part which is occupied by the rod-shaped electrode portion form openings, individually.

8. A radio knife according to claim 7, where the distal end portion of the electrode portion comprises a triangular plate arranged perpendicular to a longitudinal direction axis of the electrode portion.

* * * * *